United States Patent
Carey et al.

[11] Patent Number: 6,061,950
[45] Date of Patent: May 16, 2000

[54] BURNABLE COIL HOLDER

[75] Inventors: Michael R. Carey, Mount Pleasant; Paul E. Furner, Caledonia; Donald W. Hildebrandt, Yorkville; Amelia H. Majerowski, Kenosha; Russell H. Petersen, Mount Pleasant, all of Wis.

[73] Assignee: S. C. Johnson & Son, Inc., Racine, Wis.

[21] Appl. No.: 09/109,439

[22] Filed: Jul. 2, 1998

[51] Int. Cl.[7] .................................................. A01M 13/00
[52] U.S. Cl. .............................. 43/125; 43/127; 422/126; D11/131.1
[58] Field of Search .............................. 43/124, 125, 127, 43/144; 422/125, 126, 305; 24/297, 324, 30.5 R, 30.5 S; 243/686; 431/296, 297; 126/152 R, 152 B, 540; D11/131.1

[56] References Cited

U.S. PATENT DOCUMENTS

| | | | |
|---|---|---|---|
| 240,384 | 4/1881 | Carey | 422/126 |
| 264,068 | 9/1882 | Estes | 24/30.5 R |
| 286,572 | 10/1883 | Arzt | 431/296 |
| 395,514 | 1/1889 | Reinhardt | 431/296 |
| D. 404,459 | 1/1999 | Furner et al. | D22/122 |
| 773,145 | 10/1904 | Hollister | 422/305 |
| 801,855 | 10/1905 | Dreyfus | 422/305 |
| 1,022,491 | 4/1912 | McCarthy | 422/305 |
| 1,162,682 | 11/1915 | Cherry | 422/126 |
| 1,265,166 | 5/1918 | Bauer | 422/125 |
| 1,289,368 | 12/1918 | Berg | 431/296 |
| 1,355,696 | 10/1920 | Ross | 431/297 |
| 1,412,516 | 4/1922 | Ghosh | 422/126 |
| 1,474,910 | 11/1923 | Petersen | 431/297 |
| 1,530,103 | 3/1925 | Booth | 422/126 |
| 1,609,814 | 12/1926 | Gray et al. | 422/126 |
| 1,710,615 | 4/1929 | Gallery | 422/126 |
| 2,023,402 | 12/1935 | Brown | 422/126 |
| 2,120,204 | 6/1938 | Langhorst | 422/305 |
| 2,189,730 | 2/1940 | Esch | 43/125 |
| 2,323,804 | 7/1943 | Driscoll | 43/125 |
| 2,521,942 | 9/1950 | Pearsall | 422/305 |
| 2,765,579 | 10/1956 | Gordon | 43/127 |
| 2,770,854 | 11/1956 | Miszeika | 422/126 |
| 2,809,512 | 10/1957 | Hartnett | 431/297 |
| 3,141,221 | 7/1964 | Faulls, Jr. | 24/30.5 R |
| 3,285,694 | 11/1966 | Marchi | 422/305 |
| 3,659,373 | 5/1972 | Daeninckx | 43/125 |
| 3,754,861 | 8/1973 | Sadahiro | 43/125 |
| 3,778,924 | 12/1973 | Okui | 43/129 |
| 3,795,999 | 3/1974 | Tabita | 43/127 |
| 3,796,002 | 3/1974 | Katsuda | 43/125 |
| 4,126,958 | 11/1978 | Yokoyama | 43/127 |
| 4,324,763 | 4/1982 | Jarman | 43/125 |

(List continued on next page.)

FOREIGN PATENT DOCUMENTS

| | | | |
|---|---|---|---|
| 557990 | 5/1958 | Canada | 43/127 |
| 302471 | 2/1989 | European Pat. Off. | 43/125 |
| 909302 | 5/1946 | France . | |
| 2719192 | 11/1978 | Germany | 43/127 |
| 473815 | 8/1952 | Italy | 43/127 |
| 2276547 | 10/1994 | United Kingdom . | |

OTHER PUBLICATIONS

A Punks box side, undated, admitted prior art, entitled "outdoor Mosquito Coils", depicting a bend tab holder.

Two pages of photos (and a sketch) depicting a Pianchu mosquito coil holder, undated, admitted prior art.

*Primary Examiner*—Michael J. Carone
*Assistant Examiner*—Darren W. Ark

[57] ABSTRACT

A burnable coil holder such as a mosquito coil holder has a base member with a plurality of non-metallic support peaks and a higher central metal support spade. The spade supports the burnable coil from a single point under normal circumstances. The non-metallic support peaks provide support if the coil sags during use. The support peaks are positioned in a cross or spiral array around the spade. The spade has teeth to grip the coil, a shoulder to support the coil, and spaced legs to permit easy insertion of the spade into the base member.

16 Claims, 3 Drawing Sheets

U.S. PATENT DOCUMENTS

| | | | |
|---|---|---|---|
| 4,347,217 | 8/1982 | Radkins et al. | 422/126 |
| 4,708,851 | 11/1987 | Freytag Von Loringhoven | 422/125 |
| 4,721,455 | 1/1988 | Barfus | 431/296 |
| 4,760,624 | 8/1988 | Fish | 24/30.5 S |
| 4,765,090 | 8/1988 | Kuan et al. | 43/127 |
| 4,839,144 | 6/1989 | Martin | 43/127 |
| 4,959,925 | 10/1990 | Nelson et al. | 43/125 |
| 4,998,479 | 3/1991 | Perham et al. | 43/127 |
| 5,020,753 | 6/1991 | Green | 248/686 |
| 5,495,645 | 3/1996 | Suzuki et al. | 24/30.5 S |
| 5,647,713 | 7/1997 | Ge et al. | 24/324 |
| 5,657,574 | 8/1997 | Kandathil et al. | 43/125 |
| 5,852,850 | 12/1998 | Hanten et al. | 24/30.5 R |
| 5,907,891 | 6/1999 | Meyer | 24/297 |

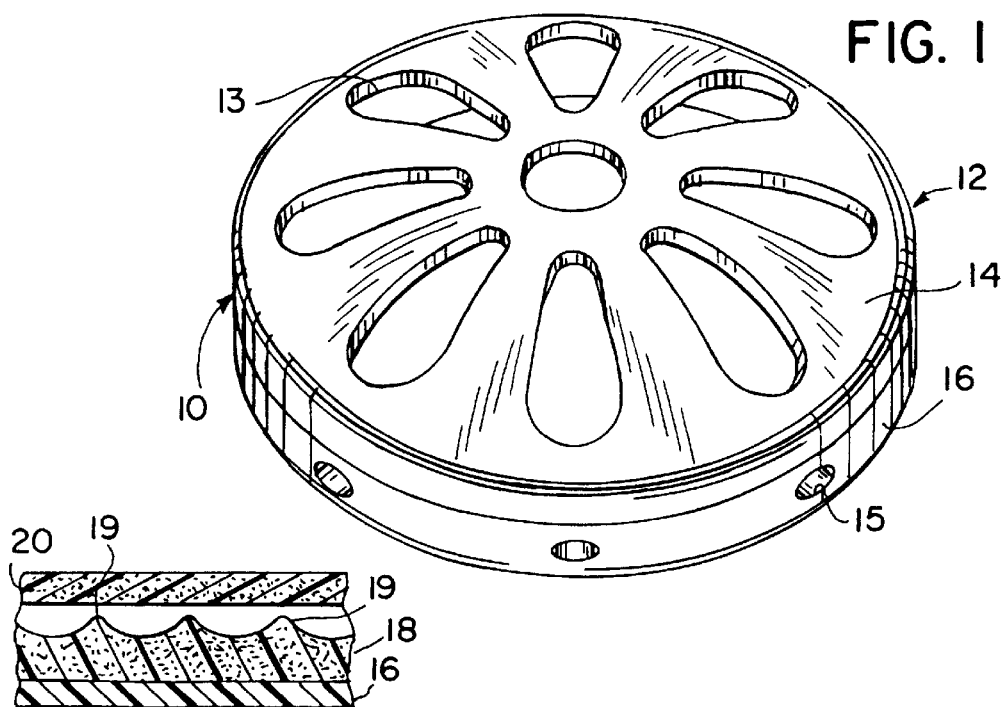
FIG. 1
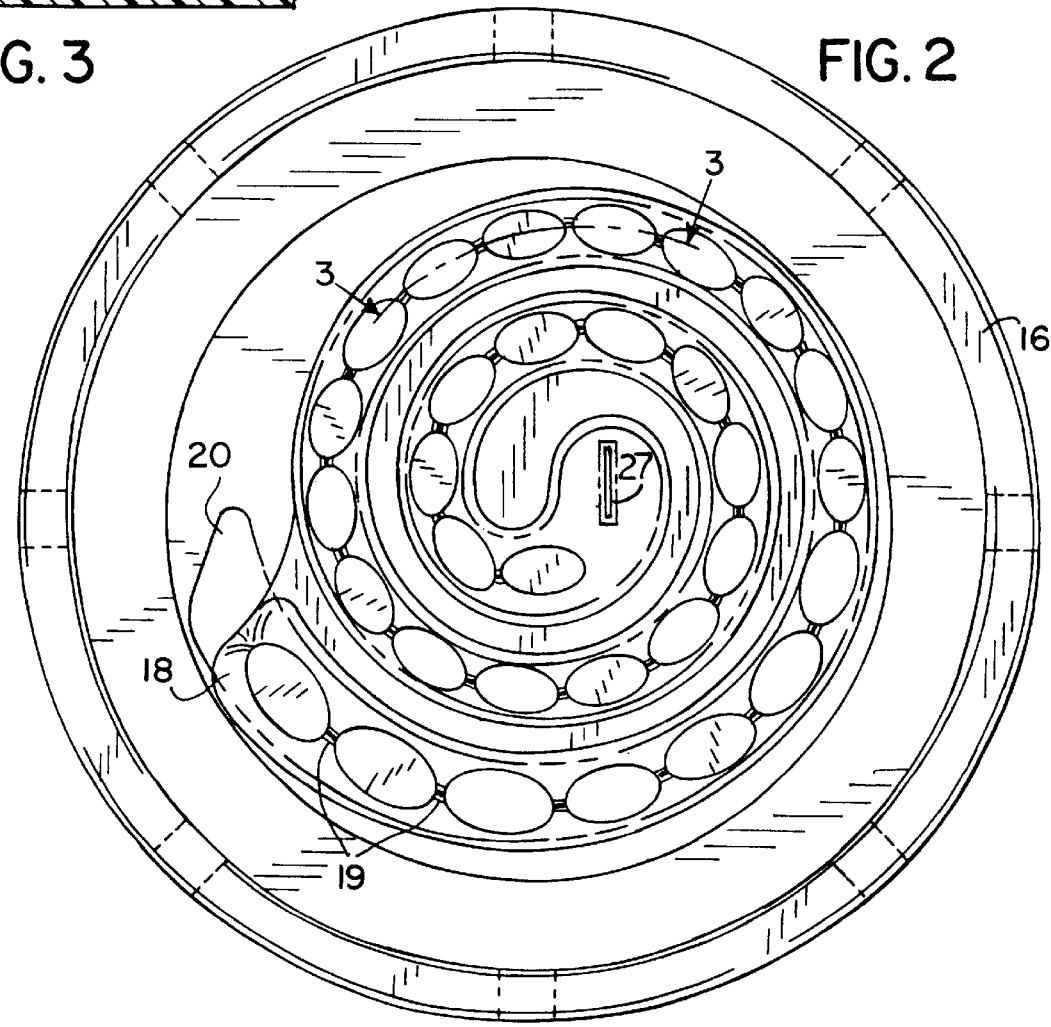
FIG. 3
FIG. 2

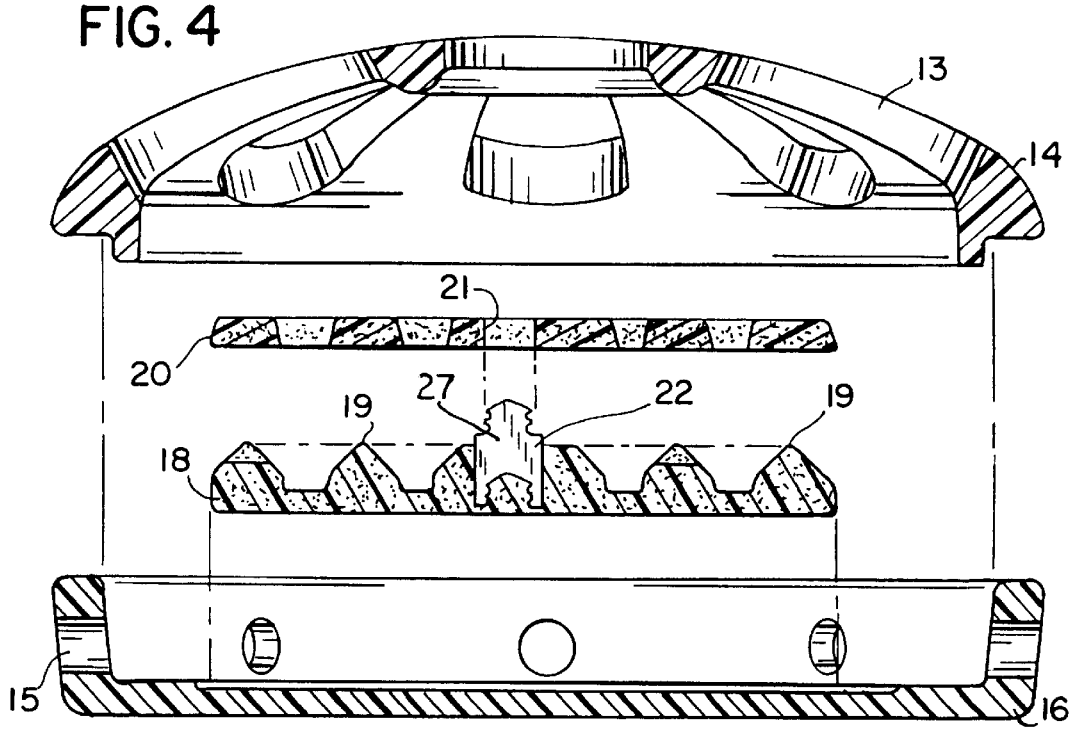
FIG. 4
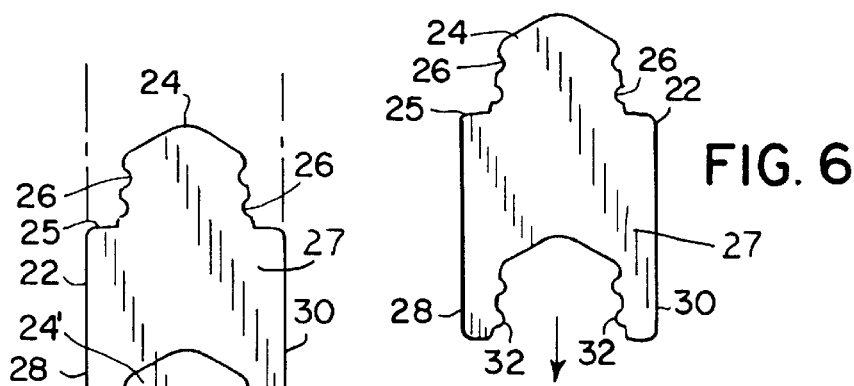
FIG. 5
FIG. 6
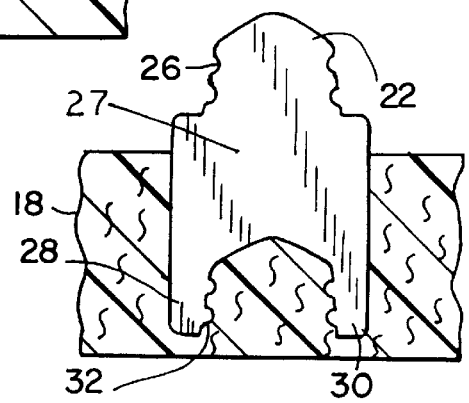
FIG. 7

BURNABLE COIL HOLDER

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to holders for burnable coils. More particularly, it relates to holders that minimize the tendency of such coils to be snuffed out during use.

Mosquito coils and other burnable coils such as incense coils are designed to burn slowly. As a result, they are somewhat susceptible to being snuffed out if they are positioned on a flat surface when they are burning. This is because such a surface can draw too much heat from the coil, slowing or even extinguishing combustion.

A variety of holders have therefore been designed to support such coils during burning. One provides a single vertical central post to support the coil. The coil is impaled on the post so that it is elevated entirely up off of whatever surface the post projects upwardly from. Because the coil is only supported at a single point by such a post and that point is the last part of the coil to be burned, the coil is usually able to burn until it reaches its end.

However, such coils are often made of materials that readily absorb humidity from the air. In highly humid conditions (such as those conditions in which mosquito coils may well be most valuable), the coils can sag when supported only from the center. This can lead to breakage or to the outside of the coil's touching a supporting flat surface, thereby snuffing the coil.

Another approach to supporting burning coils is to position the coil on a metal wire screen. See eg. U.S. Pat. No. 3,796,002. The disclosure of this patent (and of all other publications referred to herein) are incorporated by reference as if fully set forth herein. However, such screens are typically metallic and therefore good heat conductors. This can itself lead to too much heat loss from the coil which, together with the fact that a coil on a wire screen support is in contact with the screen at numerous positions, can increase the chance of the coil's being snuffed.

U.S. Pat. No. 4,126,958 uses glass fiber nets to support a mosquito coil. While the heat loss to the screen is reduced as compared to metallic screens, the coil is still in continuous contact with the net at numerous points. Also, these nets had to be clamped to a lid and body.

In U.S. Pat. No. 4,765,090 a coil is formed with integral, downwardly projecting bumps that act as integral legs to hold the coil up off of a supporting surface. However, this significantly complicates the manufacturing process for the coils.

Yet another approach is to provide a metal can whose lower base has positioned thereon an array of upwardly turned metal tabs. This approach requires the coil to rest on numerous tabs simultaneously.

It can therefore be seen that a need exists for an improved burnable coil holder.

BRIEF SUMMARY OF THE INVENTION

In one embodiment, the invention provides a burnable coil holder assembly having a base member. Extending upwardly from the base member are a spade suitable to support a burnable coil and an array of nonmetallic support peaks positioned around the spade that are suitable to support the burnable coil if the coil sags onto them. The spade extends higher than the support peaks.

The array can be in the shape of a cross having four arms, with the spade being positioned adjacent a junction between arms of the cross. Alternatively, the array can be in the shape of a spiral, with the spade being positioned adjacent a radially inward portion of the spiral. The spiral may be an array of separate support peaks that are so positioned that a line drawn sequentially outwardly from peak to peak, from the innermost peak to the next innermost and so forth, will define a rough spiral, or the spiral may be defined by one or more curving ridges, each having a single narrow, upwardly presented ridge edge that can support a sagging coil on a knife edge. The upwardly presented ridge edges are positioned to be under a correspondingly spiral shaped coil held on the spade. Other array configurations are also possible, preferably where the array has at least four of such support peaks.

The spade can be a part of a support member formed from a steel strip, the spade having a tapered upper portion adjacent to and above a plurality of outer side teeth, and a shoulder below and adjacent the outer side teeth. The support member also has one and preferably two legs below the side teeth together with additional teeth formed on an internal surface of the legs.

The base member can be a separate element, it can be an integral part of the housing bottom, or it can be used without a housing. The housing can have a cover member extendible over the housing bottom so that the coil can be hidden from view when it is burned.

The support peaks (and base member) are preferably formed of a temperature resistant material that does not readily transfer heat, such as fired terra-cotta clay, other ceramics such as other clays and porcelain, molded sand, and temperature resistant thermoplastics. The base member, housing bottom, and cover member may be cast, molded, or otherwise formed from any suitable clay, ceramic, molded sand, or plastic using manufacturing methods selected from among those well known in the art. Slip casting in terra-cotta is preferred.

In another form, the invention provides a method of supporting a burnable coil. The coil is positioned on the spade, described above, to be held above an array of support peaks, as described, above. The coil is thereby supported at only one point in normal use to minimize the likelihood of the coil being snuffed. However, if a portion of a coil should sag, it will not be permitted to sag into full contact with a flat support surface because one (or at most a few) support peaks will act as supplemental supports.

In yet another form the invention provides a spade for supporting a burnable coil. The spade has an elongated strip having a tapered upper end, a tooth along a side of the strip adjacent and below the tapered end, a support shoulder adjacent and below the tooth, and a support leg extending down from the shoulder. There are preferably two such support legs formed on the strip below the tooth, and at least one inside surface of one of the legs has a tooth formed thereon.

Other advantages of the invention will be apparent from the detailed description, below, of preferred embodiments of the invention. However, these embodiments do not represent the full scope of the invention. Rather the invention may be employed in other embodiments. Reference should therefore be made to the claims for interpreting the full breadth of the invention.

BRIEF DESCRIPTION OF THE DRAWINGS

FIG. 1 is a top perspective view of a burnable coil holder assembly of the present invention.

FIG. 2 is a top plan view showing the burnable coil holder assembly of this invention once the top cover has been removed.

FIG. 3 is a vertical sectional view taken along line 3—3 of FIG. 2.

FIG. 4 is an exploded view of the burnable coil holder assembly and housing therefor.

FIG. 5 is a front view illustrating the manufacture of a plurality of spades for use with the holder.

FIG. 6 is a front view illustrating the assembly of one such spade into a clay base member.

FIG. 7 is a view similar to FIG. 6, albeit showing the spade already inserted into the base member.

DETAILED DESCRIPTION OF THE INVENTION

Figure 8:
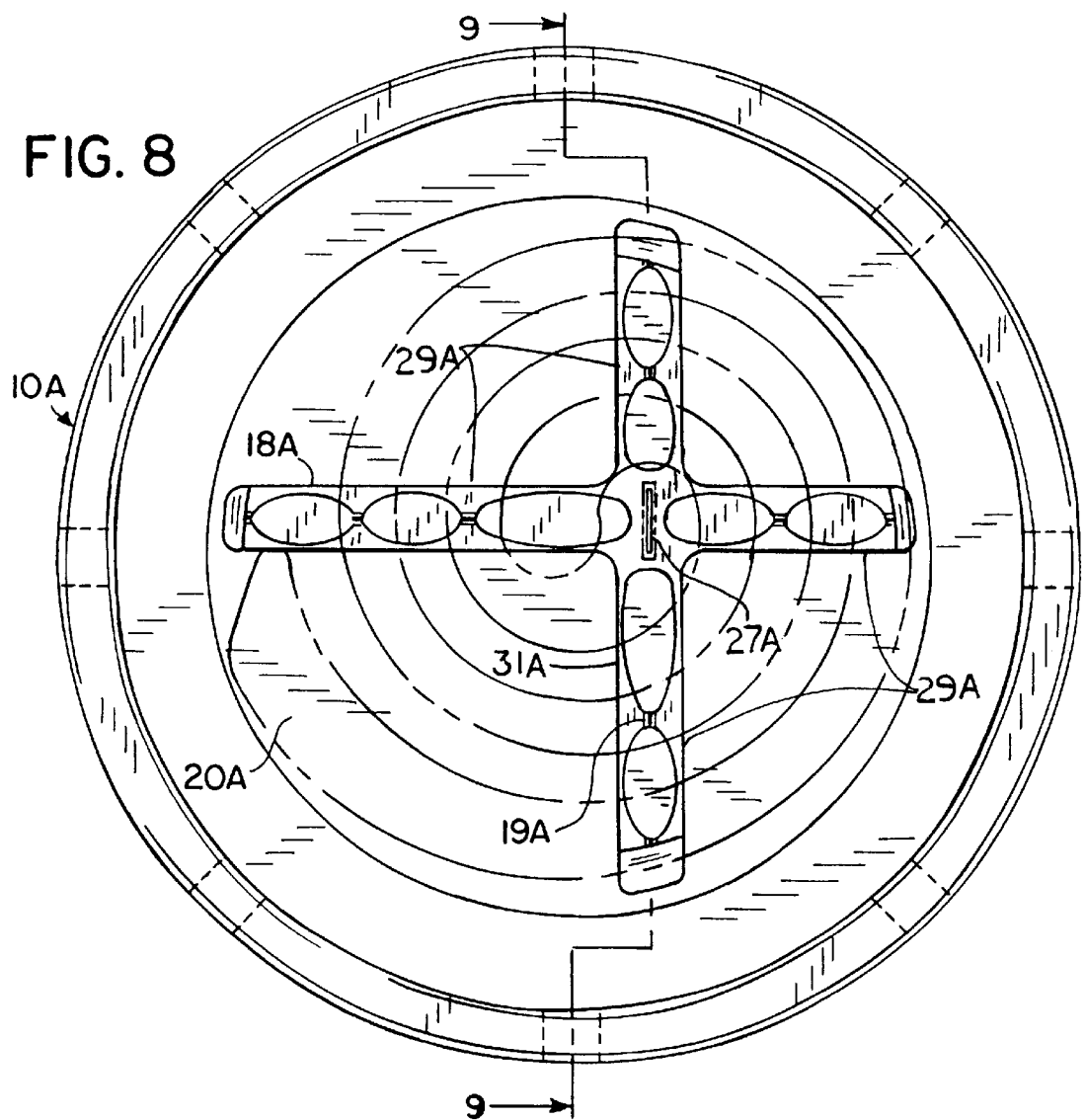
FIG. 8 is a view similar to FIG. 2, albeit illustrating a second embodiment of the invention.

The holder assembly 10 includes a housing 12 having a cover 14 and a bottom 16. A non-metallic base member 18 is positioned in the housing 12. It has a support member 27 engaged in the bottom 16. The support member 27 has a spade 22 that extends upwardly from the base member 18 for engagement with a radially inward part of a burnable coil, such as mosquito coil 20. The spade 22 has a shoulder 25 which serves as a stop for supportive engagement with the mosquito coil 20.

Coil 20 is preferably of the type disclosed in U.S. Pat. No. 5,657,574, albeit with a pre-formed slot 21 for receiving the spade. A variety of other spiral coils could be used that incorporate desired materials to be dispersed (e.g. insecticides, insect repellents, fragrances, and the like).

As best seen in FIGS. 1 and 4, the housing cover 14 and the housing bottom 16 have air passages 13 and 15 to allow air to enter and burnt vapors to exit during combustion of the mosquito coil. The cover partially hides the coil during use.

Referring specifically to FIG. 3, it is seen that the mosquito coil 20 is normally supported above base member 18 on spade shoulder 25. The base member 18 preferably is formed with a series of support peaks 19 for providing support to the mosquito coil 20 in the event that it sags downwardly as it is being burned. Preferably, the support peaks 19 terminate upwardly in a point and, for strength, preferably have a cone or pyramid shape. As particularly evident from FIG. 4, shoulder 25 of the spade 22 extends higher than the support peaks 19.

FIG. 5 shows that a series of support members 27 can be stamped from a single strip of metal so as to provide spade tapered portions 24, 24', and 24", shoulder portions 25, 25', and 25", as well as grooves 26, 26', and 26", defining teeth therebetween. The forming of the tapered portions and teeth simultaneously effect the formation of the legs corresponding to the legs 28 and 30 of the next adjacent support member in the series of support members being stamped. In a similar manner, the teeth 32 on the legs 28 and 30 provide the grooves 26' in the tapered portion 24' and the teeth 32' in the legs 28' and 30' provide the grooves 26" in the tapered portion 24". Thus, no metal is wasted as a continuous series of support members 27 are stamped from the strip of metal.

The support member 27 is seen in FIG. 6 in a position where it is about to be inserted into a clay base member 18 that has not yet been fired. The space between legs 28 and 30 allows the support member 27 to be thrust into unfired clay without displacing an excessive amount of clay adjacent to the support member. A broad, solid structure instead of the legs 28,30 would displace more clay, creating product distortion and other manufacturing problems. In the support member 27 of the invention, even though the spade 22 can be fairly wide and strong, allowing a coil to be held securely, the support member 27 is held in the clay by the relatively slender legs 28,30.

FIG. 7 shows the support member 27 embedded into base member 18. Once the clay is fired, the projecting teeth 32 provide a secure attachment of the support member 27 to the base member 18.

Figure 9:
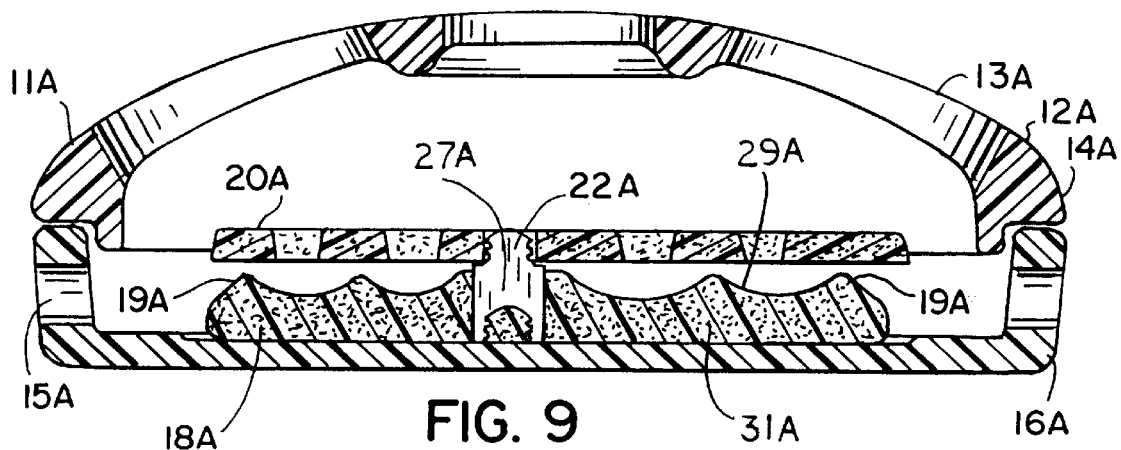
FIG. 9 is a view in cross section taken along line 9—9 of FIG. 8.

Another embodiment of the invention is shown at 10A in FIGS. 8 and 9. Similar components are shown with similar numbers (except with the suffix "A"). This embodiment differs from that previously described in that the base member 18A includes a cross-shaped sag support 31A, preferably having four cross arms 29A. The arms 29A can be of the same length, or they can be of different lengths to permit use of offset or otherwise generally non-radially symmetrical coils. A support member 27A having a spade 22A is held by the base member 18A and preferably is held at or near the junction of the arms 29A. The sag support 31 A also preferably includes a multiplicity of support peaks 19A extending upwardly relative to the base portion 18A.

An important feature of both holder assemblies 10 and 10A is the use of a base member that has an array of support peaks, preferably all non-metallic. The coil is selected and the support peaks are arrayed such that the support peaks are positioned directly under the coil at a plurality of locations. If the coil contacts the support peaks while burning, the contact will be limited preferably only to point contacts with non-metallic material, reducing the chance of a burning coil's being snuffed by the conduction of heat from the burning coil.

While specific embodiments have been shown, various modifications falling within the breadth and scope of the invention will be apparent to one skilled in the art. For example, while support member 27 has been shown with separated legs 28, 30, having the advantages discussed above, a support member could be employed without them. Also, a post-like or other shaped support member is possible. Thus, the claims should be looked to in order to understand the full scope of the invention.

INDUSTRIAL APPLICABILITY

The invention provides a burnable coil holder and techniques for using it.

We claim:

1. A burnable coil holder assembly, comprising a base member having extending upward therefrom
   a. a spade suitable to support a burnable coil, and
   b. an array of non-metallic peaks positioned around the spade that are suitable to support the burnable coil if the coil sags adjacent them;
   wherein the spade extends higher than the array of peaks; and
   wherein the spade has a tapered upper portion adjacent and above a plurality of outer side teeth, the teeth being along sides of the spade adjacent and below the tapered upper portion.

2. The holder assembly of claim 1, wherein
a. the array is in the shape of a cross having arms, and
b. the spade is positioned adjacent a junction between two arms of the cross.

3. The holder assembly of claim 2, wherein not all of the cross arms are of the same length.

4. The holder assembly of claim 1, wherein the array is in the shape of a spiral and the spade is positioned adjacent a radially inward portion of the spiral.

5. The holder assembly of claim 1, wherein the array comprises at least four of said peaks.

6. The holder assembly of claim 1, wherein the spade forms a part of a support member, the support member also including two downwardly extending legs, with teeth also formed on an internal surface of the legs.

7. The holder assembly of claim 1, wherein the spade has a support shoulder below and adjacent the outer side teeth.

8. The holder assembly of claim 1, wherein the base member is an integral part of a housing bottom.

9. The holder assembly of claim 1, further comprising a cover member extendible over the base member.

10. The holder assembly of claim 1, wherein the spade is made of metal.

11. The holder assembly of claim 1, wherein the array of peaks are formed of clay.

12. The holder assembly of claim 1, wherein the array of peaks are formed of terra cotta.

13. The holder assembly of claim 1, wherein the array of peaks are formed of a plastic capable of withstanding the heat of a burning coil.

14. An assembly of a plurality of support members for supporting a burnable coil, the assembly having been formed from a single strip of material, the assembly comprising:

a first support member for supporting a burnable coil having at a head end a spade with a tapered portion, a radially extending tooth along a side of the spade, a support shoulder adjacent the tooth but on an opposite side of the tooth from the head end, and two legs extending axially away from the shoulder and away from the head end; and a second support member having at a head end of the second support member a spade with a tapered portion, a radially extending tooth along a side of the spade of the second support member, a support shoulder adjacent the tooth of the second support member but on an opposite side of the tooth of the second support member from the head end of the second support member, and two legs extending axially away from the shoulder and head end of the second support member;

wherein at least one leg of said two legs of the first support member is interfit with the tooth of the second support member.

15. The assembly of claim 14, wherein the first support member has an identical configuration to the second support member.

16. A method of supporting a burnable coil on a holder, the holder having a base member having extending upward therefrom a spade suitable to support a burnable coil, and an array of non-metallic peaks positioned around the spade that are suitable to support the burnable coil if the coil sags adjacent them, the spade extending higher than the array of peaks, the method comprising positioning a burnable coil on the spade, above the array of peaks.

* * * * *